(12) United States Patent
Dave et al.

(10) Patent No.: US 7,177,491 B2
(45) Date of Patent: Feb. 13, 2007

(54) FIBER-BASED OPTICAL LOW COHERENCE TOMOGRAPHY

(75) Inventors: Digant P. Dave, Austin, TX (US);
Thomas E. Milner, Austin, TX (US);
Taner Akkin, Boston, MA (US)

(73) Assignee: Board of Regents the University of Texas System, Austin, TX (US)

( * ) Notice: Subject to any disclaimer, the term of this patent is extended or adjusted under 35 U.S.C. 154(b) by 213 days.

(21) Appl. No.: 10/679,952

(22) Filed: Oct. 6, 2003

(65) Prior Publication Data

US 2004/0126048 A1 Jul. 1, 2004

Related U.S. Application Data

(63) Continuation-in-part of application No. 10/044,421, filed on Jan. 11, 2002, now Pat. No. 6,665,456.

(60) Provisional application No. 60/261,658, filed on Jan. 12, 2001.

(51) Int. Cl.
*G02B 6/27* (2006.01)
*G02B 6/26* (2006.01)
*G01J 4/00* (2006.01)
*G01B 9/02* (2006.01)

(52) U.S. Cl. .......................... 385/11; 385/12; 385/15; 356/369; 356/477; 356/491

(58) Field of Classification Search ................. 385/11, 385/12, 15; 356/477–479, 491, 364, 369
See application file for complete search history.

(56) References Cited

U.S. PATENT DOCUMENTS

| | | | |
|---|---|---|---|
| 3,684,350 A | * | 8/1972 | Wentz .......................... 359/256 |
| 5,321,501 A | * | 6/1994 | Swanson et al. ............. 356/479 |
| 5,365,335 A | | 11/1994 | Sorin |
| 5,434,669 A | * | 7/1995 | Tabata et al. ................ 356/477 |
| 5,459,570 A | * | 10/1995 | Swanson et al. ............ 356/479 |
| 5,517,022 A | | 5/1996 | Bock et al. |
| 5,519,675 A | * | 5/1996 | Toofan ..................... 369/13.29 |

(Continued)

FOREIGN PATENT DOCUMENTS

WO WO 92/19930 11/1992

(Continued)

OTHER PUBLICATIONS

Schmitt, "Optical Coherence Tomography (OCT): A Review", IEEE Journal of Selected Topics in Quantum Electronics, vol. 5, No. 4, Jul./Aug. 1999, pp. 1205-1215.*

(Continued)

*Primary Examiner*—John D. Lee
(74) *Attorney, Agent, or Firm*—Gardere Wynne Sewell LLP (57) ABSTRACT

Generally, and in one form of the present invention, is a polarization-maintaining fiber-based polarization sensitive optical low coherence reflectometer for depth resolved birefringence measurement. With the present invention, linear birefringence of a sample may be measured from data recorded in a single A-Scan. In addition, the present invention provides for the simultaneous measurement of retardation and orientation of birefringent axes, wherein measured retardation is insensitive to sample rotation in the plane perpendicular to ranging.

34 Claims, 7 Drawing Sheets

U.S. PATENT DOCUMENTS

| | | | |
|---|---|---|---|
| 5,526,115 A * | 6/1996 | Nishiura | 356/460 |
| 5,559,784 A * | 9/1996 | Ota | 369/94 |
| 5,710,630 A | 1/1998 | Essenpreis et al. | |
| 5,715,334 A | 2/1998 | Peters | |
| 5,720,894 A | 2/1998 | Neev et al. | |
| 5,745,267 A | 4/1998 | Hart | |
| 5,778,016 A | 7/1998 | Sucha et al. | |
| 5,786,600 A | 7/1998 | Lambert et al. | |
| 5,795,295 A | 8/1998 | Hellmuth et al. | |
| 5,796,500 A | 8/1998 | Hart | |
| 5,847,827 A | 12/1998 | Fercher | |
| 5,920,384 A | 7/1999 | Borza | |
| 5,953,439 A | 9/1999 | Ishihara et al. | |
| 5,975,697 A | 11/1999 | Podoleanu et al. | |
| 6,134,003 A | 10/2000 | Tearney et al. | |
| 6,201,608 B1 | 3/2001 | Mandella et al. | |
| 6,208,415 B1 | 3/2001 | De Boer et al. | |
| 6,665,456 B2 * | 12/2003 | Dave et al. | 385/11 |

FOREIGN PATENT DOCUMENTS

| | | |
|---|---|---|
| WO | WO 98/38907 | 9/1998 |
| WO | WO 99/22198 | 5/1999 |

OTHER PUBLICATIONS

Rollins et al, "Optimal Interferometer Designs For Optical Coherence Tomography", Optics Letters, vol. 24, No. 21, Nov. 1, 1999, pp. 1484-1486.*
M. R. Hee et al, J.Opt. Soc. Am., B9, 903-908 (1992).
J. F. De Boer et al, Opt. Lett., 22, 934-936 (1997).
M. J. Everett et al, Opt. Lett., 23, 228-230 (1998).
M.D. Ducros et al,J.Opt. Soc. Am., A 18, 2945-2956 (2001).
C. E. Saxer et al, Opt. Lett, 25, 1355-1357 (2000).
Z. Chen et al, IEEE J. of Selected Topics in Quantum Electronics, vol. 5(4), 1134-1142 (Jul./Aug. 1999).
Z. Chen et al, Opt. Lett, vol. 22(1), 64-66 (1997).
B. H. Park et al, J. Biomed. Opt., 6:474-479 (2001).

* cited by examiner

FIBER-BASED OPTICAL LOW COHERENCE TOMOGRAPHY

CROSS-REFERENCES TO RELATED APPLICATIONS

This application claims the benefit of U.S. Provisional Patent Application No. 60/261,658, filed Jan. 12, 2001. This application is a continuation-in-part of U.S. patent application Ser. No. 10/044,421, filed Jan. 11, 2002, now issued as U.S. Pat. No. 6,665,456 and incorporated herein by reference.

BACKGROUND OF THE INVENTION

The present invention relates generally to the field of optics and in particular to an interferometric system for birefringence characterization of one or more samples.

Precise characterization of static or dynamic material birefringence is important and useful in applications that range from testing of optical components to measuring the viability and function of biologic tissue. While there are techniques that measure linear birefringence of samples, there remains a need for improved resolution and characterization, especially for samples or materials that are highly transparent, turbid and/or highly scattered. For example, fiber-based optical low-coherence reflectometry (OLCR) systems have been found to be rugged, relatively alignment-free, may be integrated with other sensing platforms and are flexible in interrogating a variety of samples. Unfortunately, fiber implementation of a polarization-sensitive OLCR system with standard single mode fiber is complicated since polarization state in a single mode fiber randomly fluctuates due to microscopic defects in the fiber, core ellipticity and external environmental perturbations. In addition, non-polarization maintaining (PM) fiber-based polarization-sensitive OLCR systems that perform birefringence characterization, work with multiple measurements and with different input polarization states to overcome the problem of fluctuating polarization state of light incident on the sample. Non-PM fiber-based setups cannot reliably measure birefringence of a sample with a single measurement even when using short lengths of fiber in the interferometer.

A technique that appears to be of more benefit for characterizing the birefringence of a sample is the polarization-sensitive optical low-coherence reflectometry (PS-OLCR). PS-OLCR is extremely useful for depth resolved birefringence characterization of transparent and highly scattering samples. With this technique, polarization maintaining single mode fibers can be used to construct a polarization-sensitive OLCR system, because the orthogonal polarization modes are isolated and preserve the input polarization state. Multiple measurements for birefringence characterization, however, limit detection of fast transient birefringence changes in a sample and are subject to any motion related artifact between multiple acquisitions. Although PM fiber based polarization-sensitive OCLR have been proposed to solve such problems, functioning and working systems have not been adequately constructed. Another disadvantage of current PM-OLCR systems is that they use bulk interferometric setups to interrogate samples for birefringence measurement. Therefore, there remains a need for a proper and efficient functioning PM-OLCR system useful for accurate birefringence characterization of a sample.

SUMMARY OF THE INVENTION

The present invention solves many problems associated with birefringence characterization, especially for samples with high scatter, turbid and/or transparent properties or of a sample in a solution with turbid or transparent properties.

The present invention is based on the use of PM fiber-based dual channel OLCR to accurately measure birefringence, aspects of which have been disclosed by the inventors, disclosures of which are incorporated herein by reference. (See Dave DP and Milner TE. Electron Lett. 2001; 37:215; Dave DP and Milner TE, Opt Lett. 2000;25: 227; both incorporated herein by reference.) In the previous disclosures, measured birefringence was sensitive to the rotation of the sample in the plane perpendicular to ranging. Here, configuration of a PM fiber-based dual channel OLCR system for birefringence characterization of one or more samples is described, wherein characterization may be made with a single measurement that is also insensitive to sample rotation.

Generally, and in one form of the present invention, is a polarization-maintaining fiber-based polarization sensitive optical low coherence reflectometer for depth resolved birefringence measurement. Unlike other fiber based polarization-sensitive optical low coherence reflectometers, linear birefringence of a sample can be measured from data recorded in a single A-Scan. Alternatively, multiple measurements may be recorded from a single sample and may provide substantially better measure of the specimen birefringence. The present invention provides for the simultaneous measurement of retardation and orientation of birefringent axes, where measured retardation is insensitive to sample rotation in the plane perpendicular to ranging.

More specifically, one form of the present invention is a fiber-based optical low-coherence reflectometer comprising a polarization-maintaining source path, reference path, sample path, and detection path, wherein the polarization-maintaining sample path is optically aligned with a collimating lens, a variable wave retarder, and a focusing lens and the focusing lens is disposed to focus light on a sample. The polarization-maintaining source path, reference path, sample path and detection paths are each connected to a polarization-maintaining path coupler. The polarization-maintaining path coupler separates light into polarization-maintaining sample and reference paths while maintaining energy separation of optical signals. The polarization-maintaining detection path is optically aligned to provide for two mutually orthogonal light beams, each capable of producing an output signal that may be detected and analyzed to provide data (e.g., birefringence data) about the sample. The sample may include a turbid or transparent sample as well as a microfluidic chip.

In another form, the invention provides for a method for characterizing birefringence of a sample comprising the steps of (1) creating a polarization-maintaining optical source path using a broadband light source; (2) creating a polarization-maintaining optical reference path that is optically coupled to a first collimator directed to an optical delay line with dispersion control; (3) creating a polarization-maintaining optical sample path that is optically coupled to a second collimator, a variable wave retarder, and a focusing lens, wherein the focusing lens focuses light on the sample; (4) creating a polarization-maintaining optical detection path optically coupled to a third collimator and a polarizing beam splitter, wherein the polarizing beam splitter is optically coupled to a first and second photodetectors that produce a first and second output signal, respectively; (5)

connecting the polarization-maintaining source path, reference path, sample path and the detection path to a polarization-maintaining path coupler; (6) converting the first and second output signals from the polarization-maintaining optical detection path with an analog-to-digital converter; and (7) connecting a processor to the analog-to-digital converter for collection of birefringent data about the sample.

As with other forms of the invention, the apparatus and method of the present invention also provides for a polarization-maintaining optical fiber sample path optically aligned with a collimating lens, a variable wave or quarter wave retarder, and a focusing lens, wherein the focusing lens is disposed to focus light on a sample to characterize birefringence about the sample with rotation insensitivity of the measured retardation of the birefringent sample and wherein light back scattered from the birefringent sample after traversing through the wave retarder is elliptically polarized. The polarization-maintaining optical fiber sample path may further comprise an optical catheter probe used for imaging and/or be configured to interrogate a sensor.

In yet another form, the present invention provides for a system of characterizing birefringence of a sample comprising a broad bandwidth optical light source; a polarization-maintaining optical source path incorporating a polarizing element that correlates optical signals in fast and slow fiber polarization channels and optically connects both channels to a polarization-maintaining path coupler; a polarization-maintaining path coupler that separates light into polarization-maintaining optical sample and reference paths while maintaining energy separation of optical signals in the fast and slow fiber polarization channels; a polarization-maintaining optical reference path optically connected to the polarization-maintaining path coupler and optically coupled to an optical delay line; a polarization-maintaining optical sample path optically connected to the polarization-maintaining path coupler, wherein the polarization-maintaining optical sample path comprises a quarter wave retarder and a focusing lens, wherein the focusing lens is disposed to focus light on the sample, said sample placed in front of the polarization-maintaining optical sample path from which birefringence is characterized; a polarization-maintaining optical detection path optically connected to the polarization-maintaining path coupler and a polarizing beam splitter that is optically coupled to a first and second photodetectors that produce first and second output signals, respectively, wherein the first and second output signals are filtered and amplified, an analog-to-digital converter connected to the filter-amplifier and a processor connected to the analog-to-digital converter. Data collected from the processor about the sample is then used to characterizing sample birefringence.

One of many advantages of the present invention is that it provides a mechanism by which to obtain additional contrast of a sample. For example, the present invention may be used to image and/or identify structural components of a sample or material, especially in materials (e.g., biologic materials) whereby functional information is associated with transient changes in birefringence. In addition, the present invention may be used to monitor, in real-time, surgical procedures, especially those that rely on photothermal injury mechanisms or changes in subsurface tissue components. The present invention may also be used as a feedback signal to control laser procedures in real time (e.g., dosimetry) and in catheters using optical fiber to deliver light.

Those skilled in the art will further appreciate the above-noted features and advantages of the invention together with other important aspects thereof upon reading the detailed description that follows in conjunction with the drawings.

BRIEF DESCRIPTION OF SEVERAL VIEWS OF THE DRAWINGS

For a more complete understanding of the features and advantages of the present invention, reference is now made to the detailed description of the invention along with the accompanying figures in which corresponding numerals in the different figures refer to corresponding parts and in which.

For a more complete understanding of the features and advantages of the present invention, reference is now made to the detailed description of the invention along with the accompanying figures in which corresponding numerals in the different figures refer to corresponding parts and in which.

DETAILED DESCRIPTION

Although making and using various embodiments of the present invention are discussed in detail below, it should be appreciated that the present invention provides many inventive concepts that may be embodied in a wide variety of contexts. The specific aspects and embodiments discussed herein are merely illustrative of ways to make and use the invention, and do not limit the scope of the invention.

In the description which follows like parts may be marked throughout the specification and drawing with the same reference numerals, respectively. The drawing figures are not necessarily to scale and certain features may be shown exaggerated in scale or in somewhat generalized or schematic form in the interest of clarity and conciseness.

Figure 1:
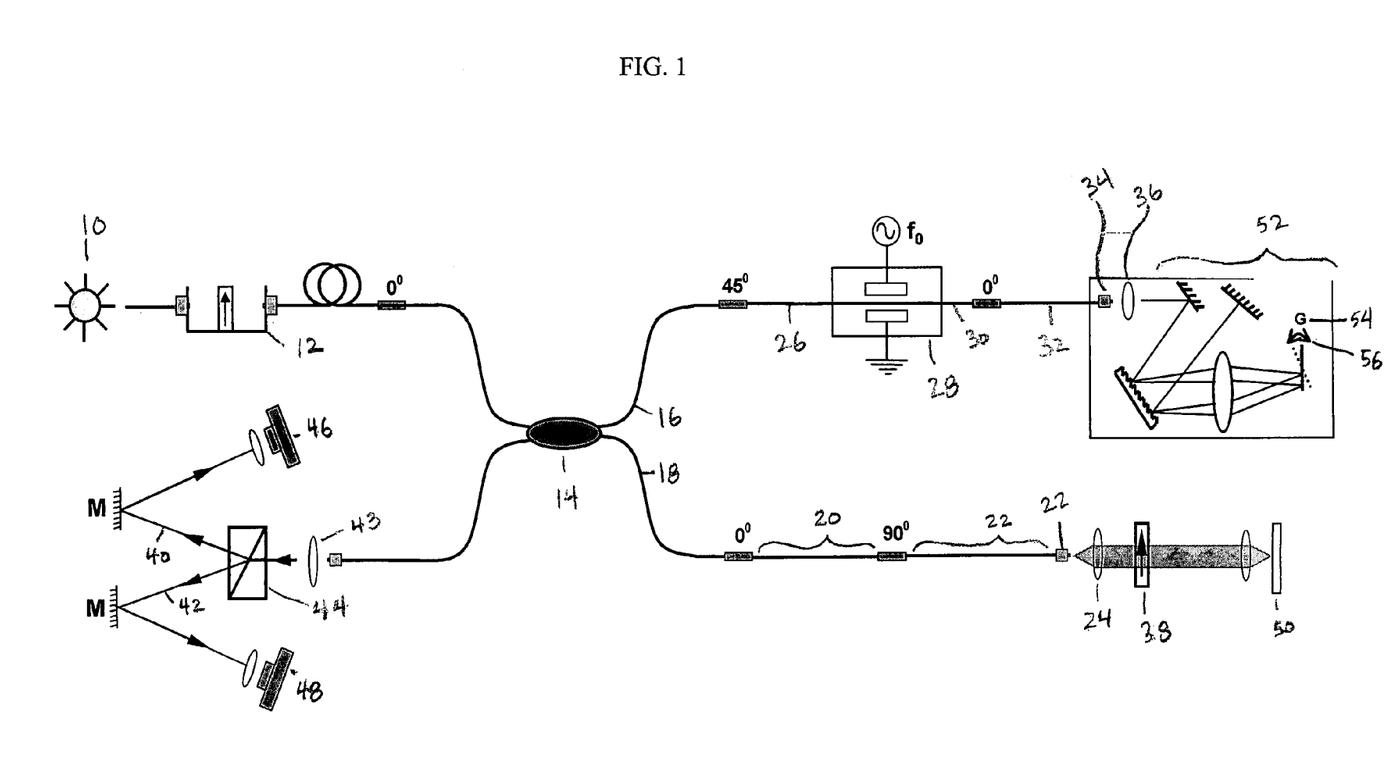
FIG. 1 depicts a schematic in accordance with one aspect of the present invention.

FIG. 1 depicts one aspect of the present invention, the PM fiber polarization-sensitive OLCR system, also referred to as the PM fiber-based polarization sensitive optical coherence tomography (PS-OCT). A light source 10 emits broadband light that is polarized by a polarizer 12 and coupled to the fast or slow axis of an input port fiber of a path coupler 14. In one embodiment, the light source includes an optical semiconductor amplifier centered at $\lambda_o=1.31$ μm with a coherence length of 24 μm. Here, the polarizer 12 is a fiber bench polarizer that polarizes the emitted light followed by its being coupled into the fast or slow axis of the input port fiber of a 2×2 PM coupler. A polarizing extension fiber spliced at 0° to the input fiber of the 2×2 PM coupler may be utilized to provide a high extinction ratio between light in orthogonal modes of the PM fiber In general, the fast and slow axes of the input port fiber form the two OLCR polarization channels, Channel 1 (Ch1) and Channel 2 (Ch2), respectively. Back reflected light from a reference path and sample path in each channel mix at the 2×2 coupler to form interference signals.

In a PM fiber interferometer, interference signals formed in Ch1 and Ch2 will overlap only if optical path-length differences between sample and reference paths for each channel are equal. As shown in FIG. 1, the length of the coupler fiber 16 in the reference path and length of the coupler fiber 18 in the sample path are equal. In addition, light in Ch1 and Ch2 travel the same optical path-length in the reference path after a 45° splice. As such, fibers attached to the coupler fiber 18 in the sample path ensure that light in Ch1 and Ch2 propagate equivalent optical path-lengths.

Owing to the birefringence of the PM fiber, any single segment of PM fiber attached to the coupler fiber in the sample path will result in unequal optical path-lengths for the two channels. Now referring to the sample path in FIG. 1, when two equal length segments of PM fiber are spliced at 90° to each other, total optical path-length traversed by light in Ch1 and Ch2 is equal. In one embodiment of the sample path, there are two segments spliced to the PM fiber: segment A and segment B. One end of segment A(20) is spliced at 0° to the coupler fiber 18 and the other end is spliced to segment B(22) at 90°. In general, the length of segment A(20) is equivalent to that of segment B(22). Here, a 90° splice interchanges the two channels, i.e., Ch1 completely couples into the Ch2 and vice-versa and provide equal path-length between channels. Segment B(22) is terminated with a connector 22 that may be an angle-cleaved connector. The connector 22 is attached to a collimator 24.

The sample path also includes a quarter wave or variable wave retarder 38, such as a achromatic quarter wave retarder, a liquid crystal variable retarder (LCVR), or possibly a short segment of PM fiber spliced at 45 degrees to the main fiber with a piezoelectric stress element to vary the birefringence. In one embodiment, the quarter wave retarder 40 is an achromatic quarter wave plate. Importantly, the quarter wave retarder provides a quarter wave of retardation to each of the OLCR source wavelengths. The quarter wave retarder or variable retarder 38 is generally aligned with its slow axis oriented at 45° to the fast or slow axis of the PM fiber so that circularly polarized light is incident on the sample. With use of a variable wave retarder, wave variation is generally is from zero to one wavelength.

A focusing lens 58 focuses the polarized light to a single point on a sample. Light back scattered from the birefringent sample after traversing through the variable wave retarder 38 is elliptically polarized.

Now referring to the reference path in FIG. 1, output of the coupler fiber 16 is spliced at 45° to the input fiber 26 of a phase modulator 28. In one embodiment, the input fiber is a PM fiber and the phase modulator 28 is a Lithium Niobate (LiNbO₃) waveguide electro-optic phase modulator. With this modulator, only light propagating along Ch2 of the input fiber 26 pigtailed to the phase modulator 28 is launched into the TE mode of the integrated optic waveguide. An output fiber 30 (e.g., PM fiber) from phase modulator 28 is spliced at 0° to a fiber segment 32 (e.g., PM fiber) that terminates with a connector 34 attached to a fiber collimator 36. The collimator 36 collimates light emitting from the optical fiber into an optical delay line with dispersion compensation.

With the present invention, collimated light from the output fiber 30 may enter an optical delay line that provides path-length modulation and compensates for dispersion imbalance in the interferometer caused by the phase modulator 28. For example, the dispersion compensating delay line may consist of a pair of diffraction gratings 54 and a movable end mirror 56. The function of the grating pair is to compensate chromatic and waveguide dispersion introduced by the phase modulator 28. If left uncompensated, dispersion increases the width of the coherence function tenfold thereby drastically reducing the longitudinal resolution of the interferometer. After a round trip, input light traveling along one fiber axis in the reference path is equally coupled to both fiber axes at the 45° splice.

Now referring to the detection path of FIG. 1, interfering light that exits the fiber is collimated by collimator 43 and split into two linearly polarized light beams or paths 40 and 42 that are mutually orthogonal from each channel by a polarizing beam splitter 44. In one embodiment, the polarizing beamsplitter is a Wollaston prism that separates the two signal channels. Each linearly polarized light path is focused into and detected by a photodetector; polarized light path 40 is detected by photo-detector 46 and polarized light path 42 is detected by photodetector 48. Photo-detectors 46 and 48 are each connected to an analog-to-digital converter (e.g., two-channel 12 bit) and signal output from each detector may be stored in computer memory for processing. The phase of each polarization channel may be determined by computing the arctangent of the filtered signal divided by its Hilbert transform.

Still referring to FIG. 1, in the detection path, interfering light is split into two mutually orthogonal linearly polarized beams from each channel by a Wollaston prism 44 (e.g., large-angle Wollaston prism) and is detected by two photodetectors 46 and 48. If the sample is a linearly birefringent material with retardation δ(z) and its fast axis is oriented at an angle θ from the horizontal, the interference intensity signals detected in Ch1 and Ch2 can be written shown below:

$$I_1(z) = k_1 \sqrt{R_x(z)} \exp[-(\Delta z/l_c)^2] \times \sin(\delta)\cos(4\pi\Delta z/\lambda_o \pm 2\theta) \quad (4)$$

$$I_2(z) = k_2 \sqrt{R_x(z)} \exp[-(\Delta z/l_c)^2 \times \cos(\delta)\cos(4\pi\Delta z/\lambda_o \quad (5)$$

where $\Delta z$ is the optical path-length mismatch between the reference and the sample paths $l_c$ is the coherence length of the source, $R_s$ is the sample's reflectivity, and $k_1$ and $k_2$ are proportionality constants that depend on the quantum efficiency of the detector and on the efficiency of light coupling into the detectors. In deriving equations (4) and (5), the light source's power spectrum is generally assumed to be Gaussian. In addition, it is assumed that the relative shift of the coherence function between two polarizations that is due to the sample's birefringence is negligible, and that the orientation of the axes remains fixed as a function of sample depth.

The phase function of the interference intensity signal in equations (4) and (5) is given by the following equation:

$$\phi_m(z) = \arctan[H[I_m(z)]/I_m(z)], \quad m=1,2 \quad (6)$$

and the amplitude function is given by:

$$A_m(z) = (\{H[I_m(z)]\}^2 + I_m(z)^2)^{1/2} \quad (7)$$

An important feature of the present invention is the ability to make a measurement of specimen birefringence using only one incident state. In addition, measurements using multiple incident polarization states may be made and will provide a substantially better measure of the specimen birefringence. To measure the birefringence using multiple incident polarization states, the present invention includes the following: (a) when using a quarter wave retarder in the sample path, it should be replaced with a variable wave retarder (e.g., a liquid crystal variable retarder or a short segment of PM fiber with external stress elements); and (b) analysis of birefringence may be generalized to the Poincaré sphere. Examples of this are provided in one of the following sections.

Figure 2:
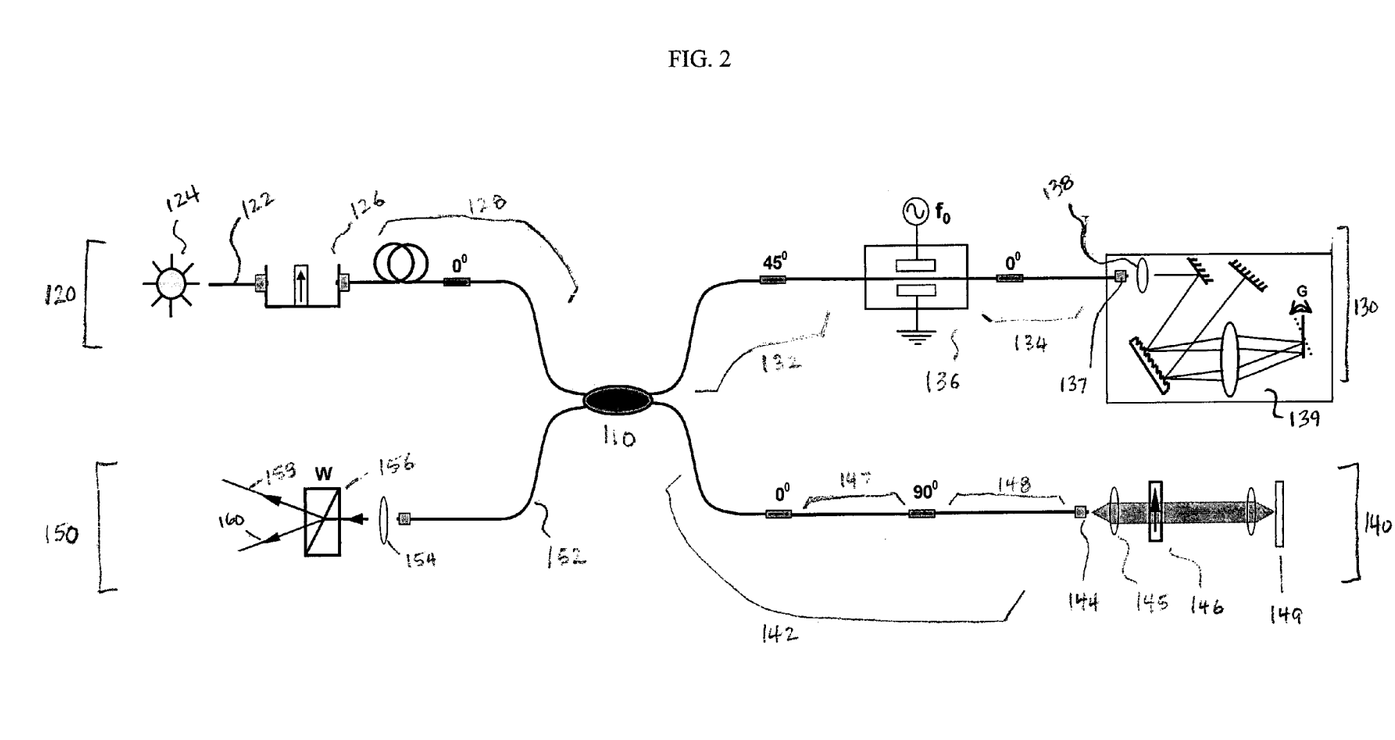
FIG. 2 depicts a schematic in accordance with another aspect of the present invention.

Now referring to FIG. 2, the present embodiment provides a fiber-based optical low-coherence reflectometer 100 comprising a path coupler 110 that separates light into a birefringent sample 140 and a reference path 130 while maintaining energy separation of optical signals in the fast and slow fiber polarization channels. As used herein, connections, alignments, optical connections and optical couplings may be used interchangeably. The reflectometer includes a source path 120 comprising a first polarization-maintaining optical fiber 122 having a first end and a second end, wherein the first end of the first polarization-maintaining optical fiber is optically coupled to a light source 124 and the second end is connected to a polarizer 126 that splits the light source into a first and second polarization channels with independent phase components. The polarizer 126 is connected to a second polarization-maintaining optical fiber 128 having a first end and a second end, the first end connected to the polarizer 126 and the second end connected to the path coupler 110. In one aspect, the polarizer output fiber is pigtailed to a polarization-maintaining optical fiber spliced at 0° with termination at the path coupler 110.

Still referring to FIG. 2, the reference path 130 comprises a third polarization-maintaining optical fiber 132 and fourth polarization-maintaining optical fiber 134. The third polarization-maintaining optical fiber 132 has a first end and a second end, the first end connected to the path coupler 110, the second end connected to a phase modulator 136. The fourth polarization-maintaining optical fiber 140 having a first end and a second end, the first end connected to the phase modulator 136 and the second end to a connector 137 and optically aligned with a first collimator 138 that collimates light emitting from the second end of the fourth optical fiber into an optical delay line 139. In one embodiment, the output fiber from path coupler 110 is spliced at 45° to the input fiber of phase modulator 136. In addition, the fourth polarization-maintaining optical fiber 134 is spliced at 0° before entry to connector 137.

Still referring to FIG. 2, the sample path 140 comprises a fifth polarization-maintaining optical fiber fiber 142 having a first and a second end, the first end connected to path coupler 110, the second end to a connector 144 and optically aligned with a second collimator 145 that collimates light emitting from the fifth optical fiber 142 to a variable or quarter wave retarder 146 that ends on sample 149. Sample path 140 further comprises two segments, segment A 147 and segment B 148. One end of segment A 147 is spliced at 0° to the path coupler 110 output fiber and the other end is spliced to segment B 148 at 90°. Segment B is terminated with connector 144. Fiber lengths of segments A 147 and B 148 may be equivalent. The 90° splice interchanges the two channels.

Still referring to FIG. 2, the invention also includes a detection path comprising a sixth polarization-maintaining optical fiber 152 having a first end and a second end, the first end connected to the path coupler 110, the second end aligned with a third collimator 154 that collimates light emitting from the sixth optical fiber 152 onto a polarizing beam splitter 156. The polarizing beam splitter 156, such as a Wollaston prism, splits the light from the sixth polarization-maintaining optical fiber 152 into a first beam 158 and a second beam 160 that are mutually orthogonal and capable of producing a first and second output signal.

In another aspect of the present invention, the first output signal is provided by a first photodetector that detects light from the first beam; the second output signal is provided by a second photodetector that detects light from the second beam. As such, a first output signal pass from the first photodetector and a second output signal pass from the second photodetector, each pass through a bandpass filter and amplifier to produce a first and a second filtered signal, respectively. The two photodetectors are connected to an analog-to-digital converter (e.g., two-channel 12 bit) and the first and second filtered signals from the analog-to-digital converter are analyzed immediately or stored in a processor (e.g., as computer memory) for later processing. Frequency multiplexed signals may be separated by digital filtering and the phase of each frequency channel is calculated by computing the arctangent of the filtered signal divided by its Hilbert transform.

Examples Using the PS-OLCR System

Figure 3:
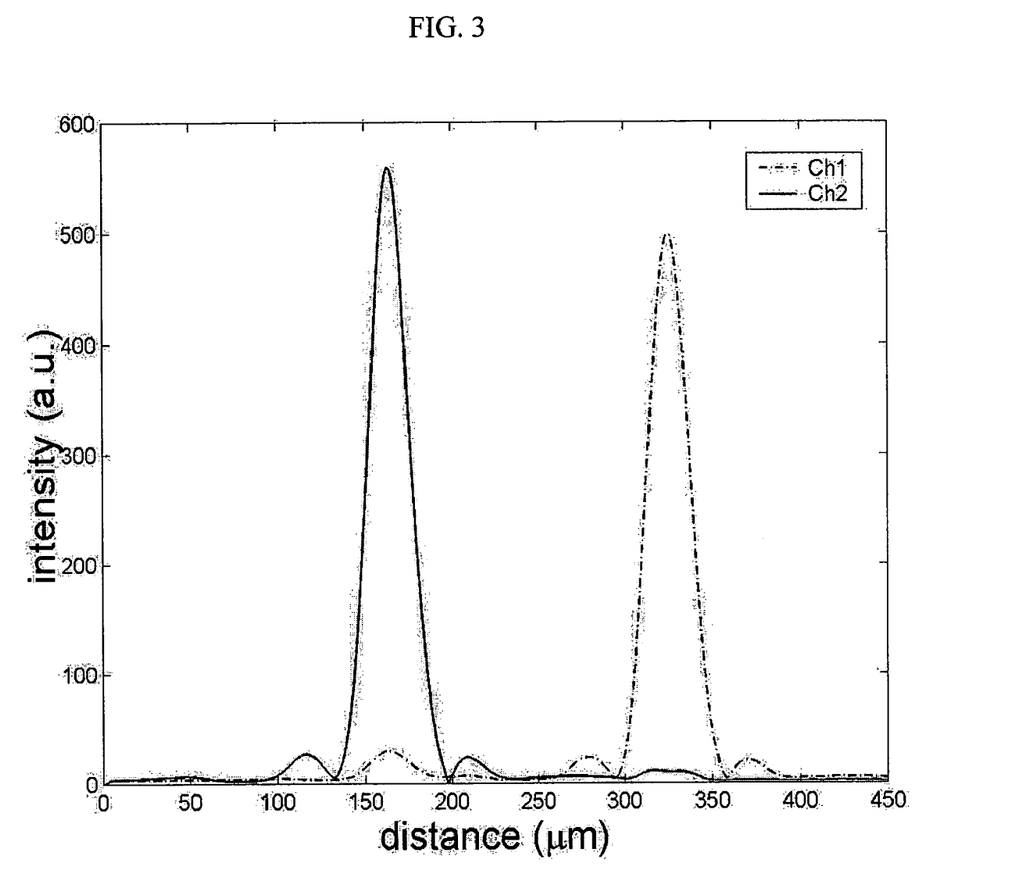
FIG. 3 depicts the demodulated interference intensity signals recorded from two surfaces of a sample at 1300 nm in accordance with one aspect of the present invention.

In one example, the PS-OLCR system uses a mica quarter wave plate (QWP) set at 1300 nm and placed as a sample. Collimated light in the sample path is focused with a 40 mm focal length achromatic doublet lens on to the sample mica QWP. Scanning in depth, interference intensity signal from the front and back surface of the 100 μm mica QWP in Ch1 and Ch2 are recorded. Demodulated amplitudes of interference intensity signals from the front and back surface of the mica QWP in each channel are shown in FIG. 3. As expected, going from front to back surface of mica QWP, the signal completely shifts from Ch1 to Ch2. Due to the non-ideal nature of the QWPs and finite cross-coupling isolation between polarization channels in the PM fiber, residual signal is present in Ch1 and Ch2 from light reflecting from front and back surface of the mica QWP.

Figure 4:
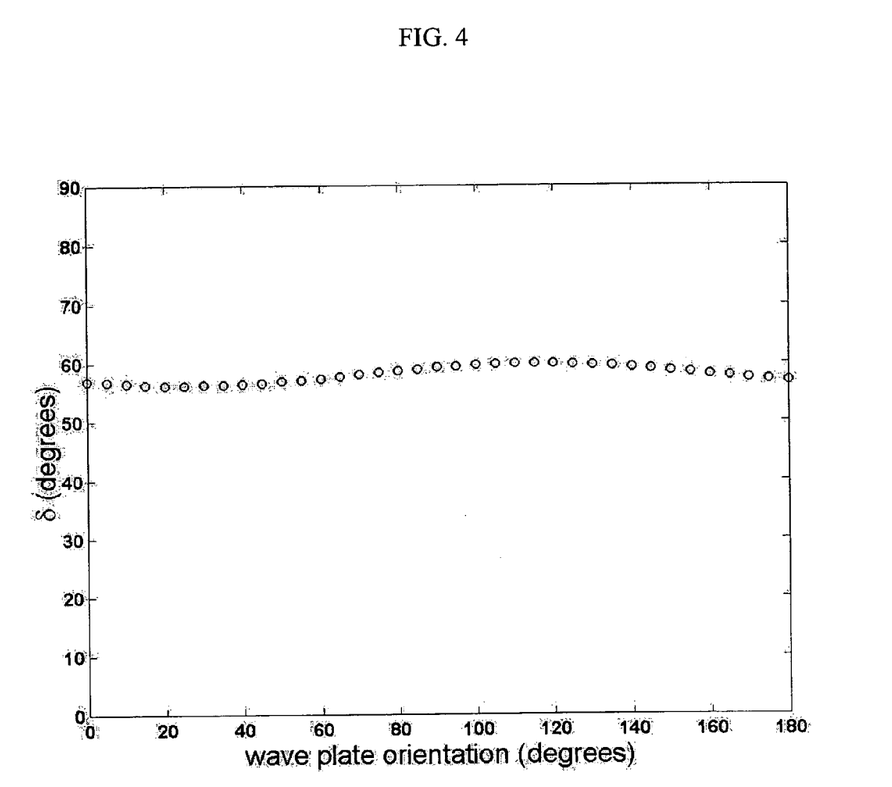
FIG. 4 depicts the measured single-pass phase retardation versus the angular rotation of a sample in accordance with one aspect of the present invention.

To demonstrate rotation insensitivity of the measured retardation of a birefringent sample a QWP at 850 nm ($\delta \approx 58°$ at 1300 nm) mounted on a rotation stage was placed in the sample path. Single-pass retardation from passage through the sample for various angular orientations was calculated. FIG. 4 shows measured phase retardation versus sample rotation from 0° to 180°, plotted in increments of 5°. Here, the average value of the measured phase retardation over the whole rotation range was 58.4° with a standard deviation of 1.2°.

Figure 5:
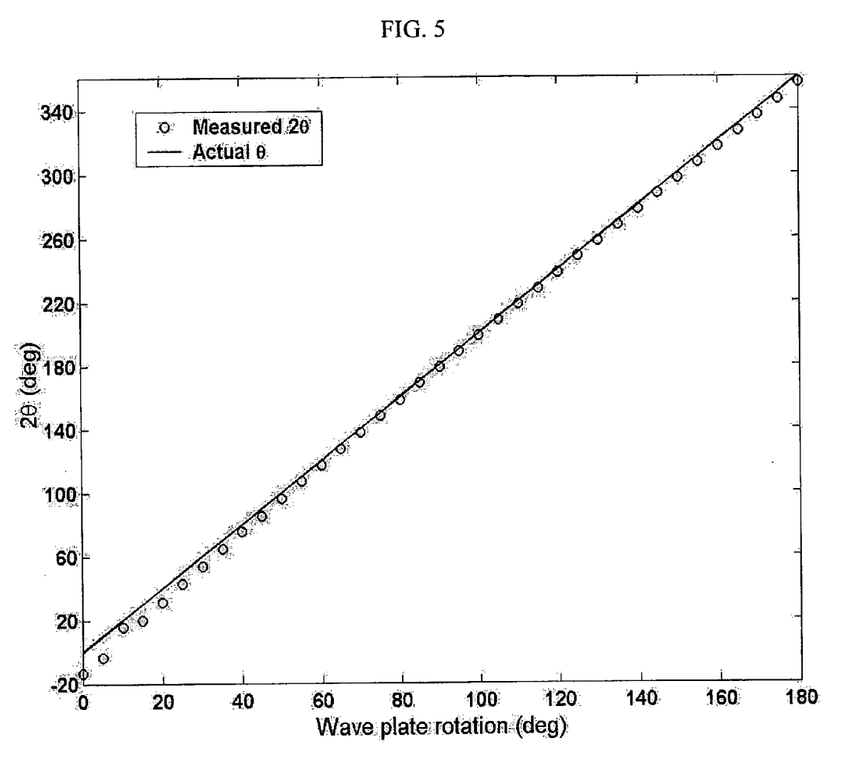
FIG. 5 depicts the measured and actual orientation of the fast axis of a sample with respect to its horizontal axis in accordance with one aspect of the present invention.

Calculating the phase difference between the two channels gives the orientation (2θ) of the slow axis of the sample with respect to the horizontal. Shown in FIG. 5 are the measured and expected values of 2θ as a function of QWP rotation. Since the PM fiber segments in the sample and reference paths are not perfectly matched, an offset phase difference exists between Ch1 and Ch2. The measured values of θ plotted in FIG. 5 have been corrected for the offset phase difference.

Non-linear Algorithm to Determine Depth-Resolved Phase Retardation

With the present invention, optical elements in the reference and sample paths systematically alter horizontal and vertical interference fringe intensities. By use of the present invention, these altered effects may be readily calibrated and corrected to determine the true polarization state of light backscattered from a sample. For example, with the reference path, mismatch of fiber length (between reference and sample paths) modify the relative amplitude ($r=A_V/A_H$) and offset the relative phase ($\phi_r=\phi_{H-V}$) of reflected light. Likewise, in the sample path, a variable wave retarder, such as a liquid crystal variable retarder, offsets the relative phase ($\phi_{H-V}$) of transmitted light by the applied retardation $\delta_{LCVR}$. Subsequence relative phase effects are corrected by multiplying the analytic signal for the horizontal interference fringe intensity by a correction factor $re^{i(\phi_r-\delta_{LCVR})}$.

Further determination of the depth-resolved phase retardation [$\Delta\delta(z,\Delta z)$] in a form-birefringent sample requires a non-linear algorithm that uses recorded data about a sample as input to estimate the pseudo fast axis orientation $F(\phi_f,\theta_f)$ and cone apex-angle ($\theta_o$). Determination of $F(\phi_f,\theta_f)$ and $\theta_o$ is problematical because recorded data about the sample is degraded by speckle noise. Moreover, because recorded data about the sample is naturally interpreted on the Poincaré sphere, underlying geometry of the problem to determine $F(\phi_f,\theta_f)$ and $\theta_o$ is spherical and a nonlinear algorithm must be applied to determine $\Delta\delta(z,\Delta z)$.

Figure 6A:
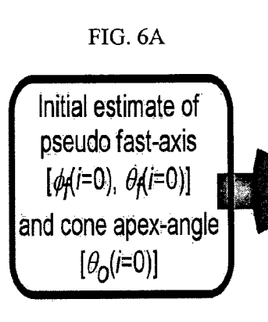
FIGS. 6A–6C depict an example of a non-linear algorithm to determine depth-resolved phase retardation in accordance with one aspect of the present invention.
Figure 6B:
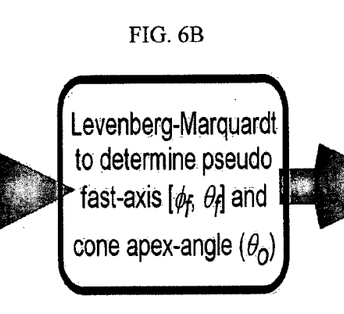
Figure 6C:
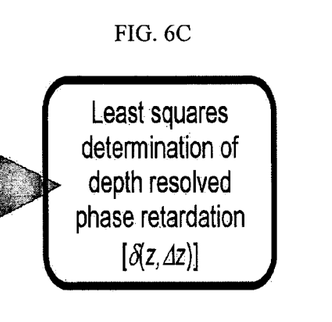

As such, the present invention provides a non-linear algorithm that consists of three components (FIG. 6): (A) initial estimate of pseudo fast axis orientation [$\phi_f(i=0),\theta_f(i=0)$] and cone apex-angle [$\theta_o(i=0)$]; (B) determination of F and $\theta_o$; and (C) computation of the depth-resolved phase retardation [$\delta(z,\Delta z)$].

Examples of Pseudo Fast Axis Orientation and Cone Apex-Angle Estimates

Because non-linear algorithms can give erroneous results when local minima exist in the residual function, determination of good initial estimates for the pseudo fast axis orientation [$\phi_f(i=0)$, $\theta_f(i=0)$] and cone apex-angle [$\theta_o(i=0)$] are important for convergence. An approach to determine [$\phi_f(i=0),\theta_f(i=0),\theta_o(i=0)$] directly from recorded data about a sample must manage the degrading effect of speckle noise.

The present invention provides a simple approach to determine an initial estimate for [$F(\phi_f,\theta_f),\theta_o$] while managing and suppressing effect of speckle noise. Normalized Stoke's parameters ($S_Q$, $S_U$, $S_V$) determined from recorded data about a sample are plotted versus depth z and fitted to a polynomial. Degree ($2^{nd}$ or $3^{rd}$) of the fitting polynomial is selected based on prior knowledge of the phase retardation ($\delta_{est}$).

Polynomials that best fit ($S_Q$, $S_U$, $S_V$) give the fitted Stoke's parameters and are denoted by [$S_{Qf}(z),S_{Uf}(z),S_{Vf}(z)$]. As used herein, phase retardation of the birefringent layer is $\delta_{est}$ and uses the fitted Stokes parameters [$S_{Qf}(z),S_{Uf}(z),S_{Vf}(z)$] to compute [$\phi_f(i=0),\theta_f(i=0),\theta_o(i=0)$]. First, the fitted Stoke's parameters [$S_{Qf}(z)$] are divided into $N_S$ equal-length ($\Delta z/N_S$) intervals where $\Delta z$ is optical thickness of the form-birefringent sample. Second, a representative Stoke's vector ($S_l$) for each interval is computed from the fitted parameters [$S_{Qf}(z),S_{Uf}(z),S_{Vf}(z)$]. Third, using $\delta_{est}$ and a pair of representative Stoke's vectors ($S_l$ and $S_m$) corresponding to intervals l and m, a fast axis ($n_{lm}$) and cone apex-angle ($\theta_{o,lm}$) are uniquely determined. By considering all pairs of representative Stokes vectors ($S_l$ and $S_m$), initial estimates of the fast axis (<n>) and cone apex-angle [$\theta_o(i=0)$] are formed by computing the weighted mean over $n_{lm}$ and $\theta_{o,lm}$ respectively (Equation 8). The weighting factor ($w_{lm}$) is given by a simple power of the relative distance (e.g., $|l-m|^{3/2}$) between l and m'th intervals.

$$\langle n \rangle = \left(\sum_{l \ne m} w_{lm} \cdot n_{lm}\right) / \sum_{l \ne m} w_{lm}, \quad \theta_o(i=0) = \left(\sum_{l \ne m} w_{lm} \cdot \theta_{o,lm}\right) / \sum_{l \ne m} w_{lm} \quad (8)$$

Initial estimates $\phi_f(i=0)$ and $\theta_f(i=0)$ corresponding to <n> are determined directly using the representation (<n>=$\sin\theta_f \cos\phi_f s_Q + \sin\theta_f \sin\phi_f s_U + \cos\theta_f s_V$) of a unit vector in spherical coordinates.

Determination of Pseudo Fast-Axis Orientation and Cone Apex-Angle

For a statistically unbiased estimate, the pseudo fast axis orientation $F(\phi_f, \theta_f)$ and cone apex-angle ($\theta_o$) must be determined using recorded data about a sample without the bias introduced by fitting.

The present invention provides a non-linear algorithm that determines an unbiased estimate of [$F(\phi_f, \theta_f), \theta_o$] by minimizing a residual function (R; Equation 9) formed by the composite sum of distances ($\epsilon_i$) on the Poincaré sphere formed between the PS-OCT data points ($S_i$) and the arc specified by [$\phi_f, \theta_f, \theta_o$]. Here, $\epsilon_i$ is the shortest distance between the i'th PS-OCT data point ($S_i$) and the arc specified by [$\phi_f, \theta_f, \theta_o$]. The distance $\epsilon_i$ is given by the angle along the great circle that is perpendicular to the arc and contains $S_i$.

$$R(\varphi_f, \theta_f, \theta_o) = \sum_i \sin^2(\varepsilon_i); \text{ where } \varepsilon_i = \cos^{-1}(S_i \cdot n(\varphi_f, \theta_f)) - \theta_o \quad (9)$$

The pseudo fast-axis $n(\phi_f, \theta_f)$ and cone apex-angle ($\theta_o$) are determined by minimizing the residual function [$R(\phi_f, \theta_f, \theta_o)$] using a Levenberg-Marquardt nonlinear algorithm. The algorithm starts with the initial estimate $\phi_f(i=0),\theta_f(i=0),\theta_o(i=o)$ derived from the fitted Stokes parameters (see previous section) and uses an iterative approach to determine $\phi_f, \theta_f, \theta_o$.

Computation of Depth-Resolved Phase Retardation

Figure 7A:
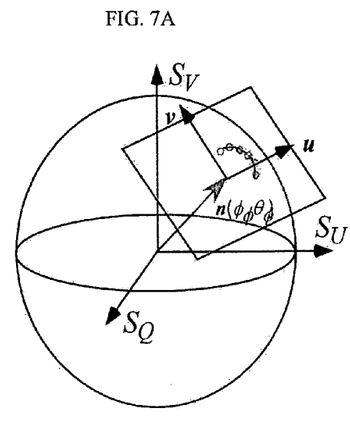
FIGS. 7A–7C depict one aspect of a procedure to determine $\delta(z,\Delta z)$ using as input, $\phi_f$, $\theta_f$, $\theta_o$ estimates determined from the Levenberg-Marquardt non-linear algorithm and recorded PS-OCT data.
Figure 7B:
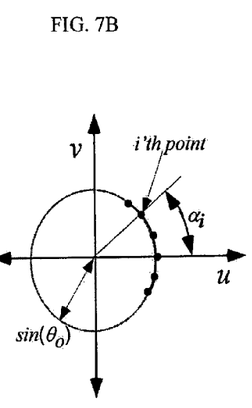
Figure 7C:
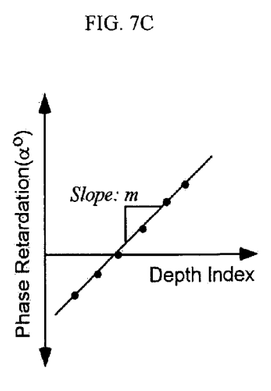

The present invention provides a procedure to determine $\delta(z,\Delta z)$ using as input, $\phi_f, \theta_f, \theta_o$, estimates determined from the Levenberg-Marquardt non-linear algorithm and recorded data about a sample ($S_i$). In this procedure, a plane is formed that is both tangent to the Poincaré sphere and perpendicular to the pseudo fast axis $n(\theta_f, \theta_f)$. Recorded PS-OCT data points ($S_i$) are projected onto the tangent plane along the line extending from the center of the sphere to $S_i$ (FIG. 7A). A right-handed orthogonal coordinate system (u,v) is defined on the tangent plane with an origin corresponding to the pseudo fast axis [F ($\phi_f, \theta_f$)] (FIG. 7B). The angle ($\alpha_i$) formed between each projected data point ($S_i$) and the u axis in the tangent plane is computed and plotted against the data point index i. Slope (m) of the linear least squares fit line to the ($i,\alpha_i$) data pairs gives the phase retardation per unit index change (FIG. 7C).

With the present invention, the depth-resolved phase retardation [$\delta(z,\Delta z)$] is given by $\delta(z,\Delta z)=N_p m$ where $N_p$ is the number of data points recorded over optical depth $\Delta z$.

Thus, the present invention is capable of depth resolved birefringence characterization with a single and with multiple measurements. The design of the reflectometer and optical coherence tomography system of the present invention places no limit on the length of fiber in the sample path as long as it is matched with proper length of PM fiber in the reference path. Inclusion of the electro-optic modulator not only provides a stable carrier frequency but also permits measurement of fast transient birefringence. Cross-coupling between PM fiber axes, either due to finite isolation or imperfect splice angle between fiber axes, may limit the dynamic range and birefringence measurement accuracy of the PM fiber based PS-OLCR instrument.

There are several advantages of the present invention that include: (a) an alignment-free system; (b) ease of use; (c) ability to integrate with other systems (e.g., microchips, sensors, catheters, lasers); and (c) an ability to probe sites that cannot be interrogated with current bulk PS-OLCR systems, such as for birefringence imaging of locations in a mammalian body. For example, the present invention may be used to probe a microfluidic chip placed in the sample path. The sample path may also consist of an optical catheter probe for imaging a sample, such a mechanical, electrical or biologic materials (e.g., an organ, tissue, or luminal wall of a coronary artery). The sample path may be configured to "read" or "interrogate" a sensor, such as a surface plasmon resonance device.

Additional objects, advantages and novel features of the invention as set forth in the description, will be apparent to one skilled in the art after reading the foregoing detailed description or may be learned by practice of the invention. The objects and advantages of the invention may be realized and attained by means of the instruments and combinations particularly pointed out here.

What is claimed is:

1. A fiber-based optical low-coherence reflectometer comprising:
    a polarization-maintaining source path;
    a polarization-maintaining reference path optically coupled to a phase modulator and an optical delay line;
    a polarization-maintaining sample path optically aligned with a collimating lens, a variable wave retarder, and a focusing lens, wherein the focusing lens is disposed to focus light on a sample; and
    a polarization-maintaining detection path,
    wherein the polarization-maintaining source path, reference path, sample path and detection path are each connected to a polarization-maintaining path coupler.

2. The fiber-based optical low-coherence reflectometer of claim 1, wherein the polarization-maintaining path coupler separates light into polarization-maintaining sample and reference paths while maintaining energy separation of optical signals.

3. The fiber-based optical low-coherence reflectometer of claim 1, wherein the polarization-maintaining source path comprises:
    a first polarization-maintaining fiber having a first end and a second end, wherein the first end of the first polarization-maintaining fiber is coupled to a light source and the second end is connected to a polarizer that splits the light source into a first and second polarization channels with independent phase components; and
    a second polarization-maintaining fiber having a first end and a second end, the first end connected to the polarizer and the second end connected to the polarization-maintaining path coupler.

4. The fiber-based optical low-coherence reflectometer of claim 3, wherein the light source is a broadband light source.

5. The fiber-based optical low-coherence reflectometer of claim 3, wherein the light source is an optical semiconductor amplifier.

6. The fiber-based optical low-coherence reflectometer of claim 3, wherein the polarizer is a fiber bench polarizer.

7. The fiber-based optical low-coherence reflectometer of claim 1, wherein the polarization-maintaining reference path comprises:
    a third polarization-maintaining fiber having a first end and a second end, the first end connected to the polarization-maintaining path coupler, the second end connected to the phase modulator; and
    a fourth polarization-maintaining fiber having a first end and a second end, the first end connected to the phase modulator, the second end to a connector and optically aligned with a first collimator that collimates light emitting from the second end of the fourth polarization-maintaining fiber into an optical delay line.

8. The fiber-based optical low-coherence reflectometer of claim 7, wherein the polarization-maintaining sample path further comprises a fifth polarization-maintaining fiber having a first and a second end, the first end connected to the polarization-maintaining path coupler, the second end to a connector and optically aligned with a second collimator that collimates light emitting from the second end of the fifth polarization-maintaining fiber to the variable wave retarder and the focusing lens.

9. The fiber-based optical low-coherence reflectometer of claim 8, wherein the connector is an angle-cleaved connector.

10. The fiber-based optical low-coherence reflectometer of claim 7, wherein the polarization-maintaining detection path comprises:
    a sixth polarization-maintaining fiber having a first end and a second end, the first end connected to the polarization-maintaining path coupler, the second end aligned with a third collimator that collimates light emitting from the sixth polarization-maintaining fiber onto a polarizing beam splitter, wherein the polarizing beam splitter splits light from the sixth polarization-maintaining fiber into a first beam and a second beam that are mutually orthogonal and capable of producing a first and second output signal.

11. The fiber-based optical low-coherence reflectometer of claim 10, wherein the first beam of the detection path is detected by a first photodetector and produces the first output signal and the second beam of the detection path is detected by a second photodetector and produces the second output signal.

12. The fiber-based optical low-coherence reflectometer of claim 7, wherein the optical delay line includes a diffraction grating and dispersion control.

13. The fiber-based optical low-coherence reflectometer of claim 7, wherein the phase modulator is a Lithium Niobate waveguide electro-optic phase modulator.

14. The fiber-based optical low-coherence reflectometer of claim 7, wherein the phase modulator provides a stable carrier frequency and permits measurement of fast transient birefringence.

15. The fiber-based optical low-coherence reflectometer of claim 1, wherein the polarization-maintaining detection path further comprises:
    a first and second output signal pass from a first and second photodetector, each output signal pass having a bandpass filter and amplifier to produce a first and a second filtered signal;
    an analog-to-digital converter connected to the bandpass filter-amplifier; and
    a processor connected to the analog-to-digital converter.

16. The fiber-based optical low-coherence reflectometer of claim 15, wherein the analog-to-digital converter is a two channel 12-bit analog-to-digital converter.

17. The fiber-based optical low-coherence reflectometer of claim 1, wherein variation of the variable wave retarder is from zero to one wavelength.

18. The fiber-based optical low-coherence reflectometer of claim 1, wherein back reflected light from the polarization-maintaining reference and sample path mix at the path coupler to form interference signals.

19. The fiber-based optical low-coherence reflectometer of claim 1, wherein the fiber-based optical low-coherence reflectometer is used to characterize birefringence of samples selected from the group consisting of a turbid sample, transparent sample, and microfluidic chip.

20. The fiber-based optical low-coherence reflectometer of claim 1, wherein light back scattered from the sample after traversing through the variable wave retarder is elliptically polarized.

21. The fiber-based optical low-coherence reflectometer of claim 1, wherein the fiber-based optical low-coherence reflectometer is rotationally insensitive of the measured retardation of a birefringent sample.

22. The fiber-based optical low-coherence reflectometer of claim 1, wherein the polarization-maintaining sample path includes two spliced segments, a first segment that is spliced at 0 degrees to a polarization-maintaining sample path fiber and a second segment that is spliced to the first segment at 90 degrees.

23. A method for characterizing birefringence of a sample comprising the steps of:
creating a polarization-maintaining optical source path using a broadband light source;
creating a polarization-maintaining optical reference path that is optically coupled to a first collimator directed to an optical delay line with dispersion control;
creating a polarization-maintaining optical sample path that is optically coupled to a second collimator, a variable wave retarder, and a focusing lens, wherein the focusing lens focuses light on the sample;
creating a polarization-maintaining optical detection path optically coupled to a third collimator and a polarizing beam splitter, wherein the polarizing beam splitter is optically coupled to a first and second photodetectors that produce a first and second output signal, respectively;
connecting the polarization-maintaining source path, reference path, sample path and the detection path to a polarization-maintaining path coupler;
converting the first and second output signals from the polarization-maintaining optical detection path with an analog-to-digital converter; and
connecting a processor to the analog-to-digital converter for collection of birefringent data about the sample.

24. The method of claim 23, wherein the first and second output signals from the polarization-maintaining optical detection path initially pass through a bandpass filter and amplifier to produce a first and second filtered signals.

25. The method of claim 23, wherein birefringent data about the sample is selected from the groups consisting of retardation and orientation of the birefringent axes of sample and depth resolved birefringence.

26. The method of claim 23, wherein birefringence is characterized with a single or multiple measurements.

27. A polarization-maintaining optical fiber sample path optically coupled to a phase modulator and an optical delay line and aligned with a collimating lens, a variable wave retarder, and a focusing lens, wherein the focusing lens is disposed to focus light on a sample to characterize birefringence about the sample with rotation insensitivity of the measured retardation of the birefringent sample.

28. The polarization-maintaining optical fiber sample path of claim 27 further comprising an optical catheter probe used for imaging.

29. The polarization-maintaining optical fiber sample path of claim 27 configured to interrogate a sensor.

30. A polarization-maintaining optical fiber sample path optically coupled to a phase modulator and an optical delay line and aligned with a collimating lens, a quarter wave retarder, and a focusing lens, wherein the focusing lens is disposed to focus light on a sample and light back scattered from the birefringent sample after traversing through the quarter wave retarder is elliptically polarized.

31. A method of optically analyzing a sample comprising the steps of:
placing a sample in front of a polarization-maintaining optical sample path that is optically coupled to a phase modulator, a first collimator, a variable wave retarder, and a focusing lens, wherein the focusing lens is disposed to focus light on the sample;
creating a polarization-maintaining optical source path to introduce light;
creating a polarization-maintaining optical reference path that is optically coupled to a second collimator, wherein the collimator is directed into a rapid scanning delay line to be used as a reference; and
detecting light changes on the sample using a polarization-maintaining optical detection path optically coupled to a third collimator and a polarizing beam splitter, wherein the polarizing beam splitter is optically coupled to a first and second photodetectors that produce a first and second output signals, respectively, wherein the first and second output signals are filtered and converted with an analog-digital converter to digital data about the sample;
wherein the polarization-maintaining optical source path, reference path, sample path and detection path are connected to a polarization-maintaining path coupler.

32. A system of characterizing birefringence of a sample comprising:
a broad bandwidth optical light source;
a polarization-maintaining optical source path incorporating a polarizing element and correlates optical signals in fast and slow fiber polarization channels and optically connects both channels to a polarization-maintaining path coupler;
a polarization-maintaining path coupler that separates light into polarization-maintaining optical sample and reference paths while maintaining energy separation of optical signals in the fast and slow fiber polarization channels;
a polarization-maintaining optical reference path optically connected to the polarization-maintaining path coupler and optically coupled to a phase modulator and an optical delay line;
a polarization-maintaining optical sample path optically connected to the polarization-maintaining path coupler, wherein the polarization-maintaining optical sample path comprises a quarter wave retarder and a focusing lens, wherein the focusing lens is disposed to focus light on the sample;
said sample placed in front of the polarization-maintaining optical sample path from which birefringence is characterized;
a polarization-maintaining optical detection path optically connected to the polarization-maintaining path coupler and a polarizing beam splitter that is optically coupled to a first and second photodetectors that produce first and second output signals, respectively, wherein the first and second output signals are filtered and amplified;

an analog-to-digital converter connected to the filter-amplifier; and a processor connected to the analog-to-digital converter.

33. A fiber-based optical low-coherence reflectometer comprising:

a path coupler that separates light into sample and reference paths while maintaining energy separation of optical signals into fast and slow fiber polarization channels;

a source path comprising a first polarization-maintaining optical fiber having a first end and a second end, wherein the first end of the first optical fiber is coupled to a light source and the second end is connected to a polarizer that splits the light source into a first and second polarization channels with independent phase components; and a second polarization-maintaining optical fiber having a first end and a second end, the first end connected to the polarizer and the second end connected to the path coupler;

a reference path comprising a third and fourth polarization-maintaining optical fiber, the third polarization-maintaining optical fiber having a first end and a second end, the first end connected to the path coupler, the second end connected to a phase modulator; and a fourth polarization-maintaining optical fiber having a first end and a second end, the first end connected to the phase modulator, the second end to a connector and optically aligned with a first collimator that collimates light emitting from the second end of the fourth polarization-maintaining optical fiber into an optical delay line;

a sample path comprising a fifth polarization-maintaining optical fiber having a first and a second end, the first end connected to the path coupler, the second end to a connector and optically aligned with a second collimator that collimates light emitting from the second end of the fifth polarization-maintaining optical fiber to a variable wave retarder and a focusing lens, wherein the focusing lens is aligned to focus light on a sample; and a detection path comprising a sixth polarization-maintaining optical fiber having a first end and a second end, the first end connected to the path coupler, the second end aligned with a third collimator that collimates light emitting from the sixth polarization-maintaining optical fiber onto a polarizing beam splitter, wherein the polarizing beam splitter splits the light from the sixth polarization-maintaining optical fiber into a first beam and a second beam that are mutually orthogonal and capable of producing a first and second output signal about the sample.

34. A fiber-based optical low-coherence reflectometer comprising:

a polarization-maintaining source path;

a polarization-maintaining reference path comprising a first polarization-maintaining fiber having a first end and a second end, the first end connected to a polarization-maintaining path coupler, the second end spliced at 45 degrees to a phase modulator and a second polarization-maintaining fiber having a first end and a second end, the first end connected to the phase modulator, the second end to a connector and optically aligned with a first collimator that collimates light emitting from the second end of the second polarization-maintaining fiber into an optical delay line;

a polarization-maintaining sample path optically aligned with a collimating lens, a variable wave retarder, and a focusing lens, wherein the focusing lens is disposed to focus light on a sample; and a polarization-maintaining detection path, wherein the polarization-maintaining source path, reference path, sample path and detection path are each connected to the polarization-maintaining path coupler.

* * * * *

UNITED STATES PATENT AND TRADEMARK OFFICE
CERTIFICATE OF CORRECTION

PATENT NO. : 7,177,491 B2
APPLICATION NO. : 10/679952
DATED : February 13, 2007
INVENTOR(S) : Digant P. Dave, Thomas E. Milner and Taner Akkin It is certified that error appears in the above-identified patent and that said Letters Patent is hereby corrected as shown below:

Col. 4, lines 13-18, delete the entire paragraph provided in duplicate, the paragraph beginning with the phrase "For a more complete" and ending with the prhase "and in which:";

Col. 6, line 64, delete "equation (7) and replace with an equation exactly as written below:

$$-- A_m(z) = (\{H[I_m(z)]\}^2 + [I_m(z)]^2)^{1/2} --$$

(7)--

Col. 9, line 53, delete the entire bracketed text that is written as " $[S_{Qf}(z)]$ " and replace with the text, including brackets, exactly as written below:

$$-- [S_{Qf}(z), S_{Uf}(z), S_{Vf}(z)] --$$

Signed and Sealed this

Nineteenth Day of June, 2007

JON W. DUDAS
*Director of the United States Patent and Trademark Office*